United States Patent [19]
Ramadoss et al.

[11] Patent Number: 6,002,024
[45] Date of Patent: Dec. 14, 1999

[54] PROCESS FOR THE ISOLATION OF 14β-HYDROXY-10-DEACETYL BACCATIN-III

[75] Inventors: Sunder Ramadoss, New Delhi; Anand Vardhan, Delhi, both of India

[73] Assignee: Dabur Research Foundation, Ghaziabad, India

[21] Appl. No.: 09/212,321

[22] Filed: Dec. 15, 1998

[30] Foreign Application Priority Data

Jul. 27, 1998 [IN] India ............................... 2194/DEL/98

[51] Int. Cl.⁶ .................................................. C07D 305/14
[52] U.S. Cl. .............................................................. 549/510
[58] Field of Search ................................................ 549/510

[56] References Cited

U.S. PATENT DOCUMENTS 5,453,520 9/1995 Bombardelli et al. .................. 549/510

*Primary Examiner*—Amelia Owens
*Attorney, Agent, or Firm*—Ladas & Parry

[57] ABSTRACT

Novel process for isolation of 14β-hydroxy 10-deacetyl baccatin-III (14β-OH-DAB) on a commercial scale from plant extract by solvent crystallization without employing chromatographic separation.

16 Claims, 1 Drawing Sheet

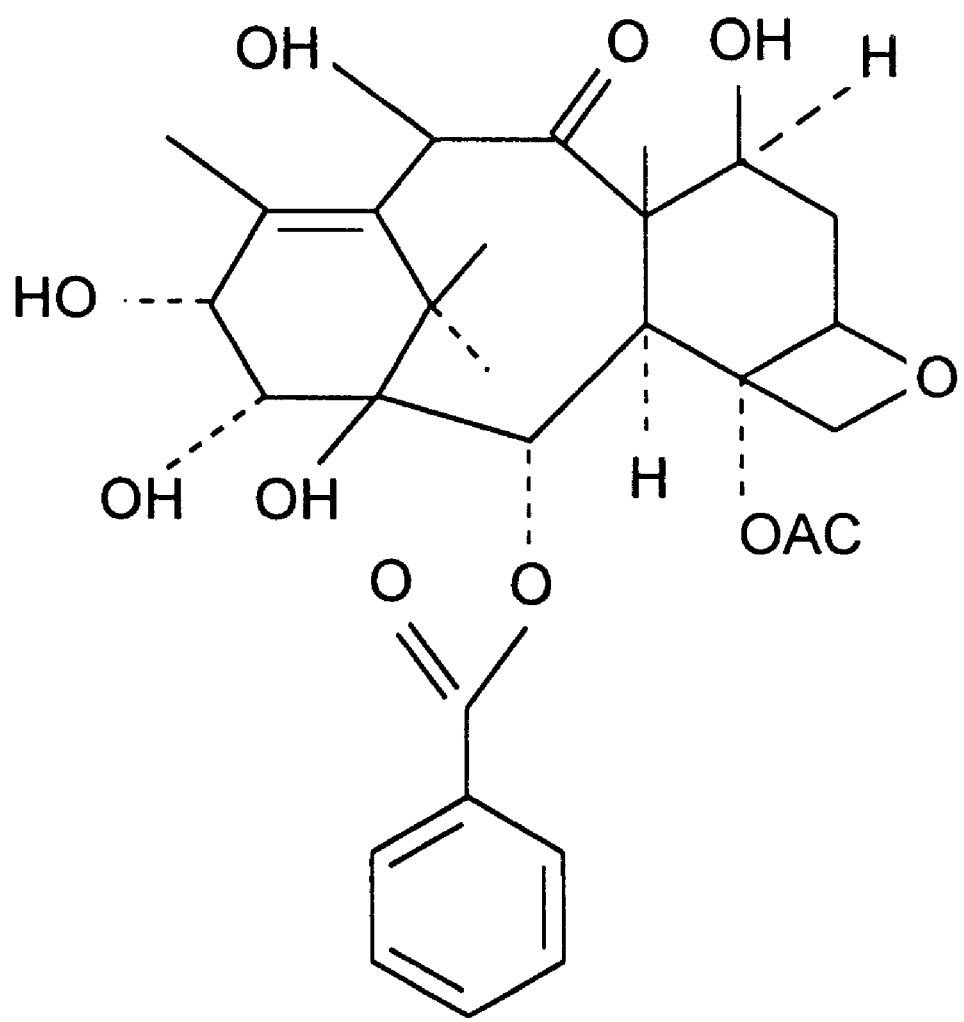
F I G. 1

PROCESS FOR THE ISOLATION OF 14β-HYDROXY-10-DEACETYL BACCATIN-III

FIELD OF THE INVENTION

The present invention relates, generally, to the field of phyto-chemistry. More specifically, the invention provides a simple and cost-effective method for the isolation of 14β-hydroxy-10-deacetyl baccatin-III (14β-OH-DAB) which is shown in the accompanying drawing, from the leaves of Taxus species, preferably *Taxus baccata*. 14β-OH-DAB is an important intermediate compound useful in the preparation of 14β-OH paclitaxel and its analogues.

BACKGROUND OF THE INVENTION

The present invention provides a solvent based process for the isolation of 14β-hydroxy-10-deacetyl baccatin-III (14β-OH-DAB) which is a very important precursor for the synthesis of 14β-hydroxy-paclitaxel analogues which show excellent cytotoxicity against human ovaries, lungs, colon and breast cancer cell hives [ref. J. Med. Chem. 1977, 40, 267–278]. Several derivatives show manifold better activity than those of paclitaxel and docetaxel.

14β-OH-10-deacetyl baccatin-III is represented by the structural formula shown in the accompanying drawing.

Prior Art References

In this field, European Patent No.0 559 019 A1 relates to isolation of 14-beta-hydroxy-10-deacetyl-baccatin III. However, the above process involves a tedious step of chromatography which adds to the cost of the process in comparison to the present process.

Another prior U.S. Pat. No. 5,453,520 discloses preparation of 14-beta-hydroxy-10-deacetylbaccatin III and its derivatives as antitumor agents. However, this Patent discloses alcoholic extraction of *Taxus wallichiana* leaves and does not disclose the novel sequence of isolating 14-beta-hydroxy-10-deacetyl-baccatin III including the selective crystallisation employed in the present invention.

Yet another Patent No. WO 9629321 A1 discloses 10-deacetylbaccatin III and 14.-beta.-hydroxy 10-deacetyl baccatin III derivatives and pharmaceutical compositions containing them. However, the above patent does not indicate or even envisage the novel sequence of steps including selective crystallisation claimed in the present invention.

Still another Patent No. EP 559019 A1 discloses preparation of 14-.beta-hydroxy-10-deacetylbaccatin III and its derivatives as antitumor agents. However, the process defined in the above patent is different and involves a costly and tedious chromatographic technique which is not employed in the present invention.

In fact, the applicants have identified that the presence of an additional C-14 hydroxyl group in 14β-OH-10-DAB is found to provide much higher solubility in protic solvents than the usual 10-DAB-III. Hence, the taxoids derived from 14β-OH-10-DAB have substantially improved solubility, bioavailability and hydrophilicity related drug resistance.

As such, the derivatives of 14β-hydroxy-10-deacetyl baccatin-III are expected to have substantially improved water solubility with consequent advantages in connection with administration by perfusion in humans of antitumour drugs containing this type of diterpenic nucleus.

OBJECTS OF THE PRESENT INVENTION

Accordingly, one objective of the present invention is to provide a simple and cost-effective process for the isolation of 14βOH-10-DAB (14β-OH-10deacetylbaccatin-III) for use as a precursor for the synthesis of 14β-hydroxy paclitaxel analogues.

One more objective of the present invention is to provide a process which does not involve tedious chromatographic technique at any stage of this process.

Yet another objective of the present invention is to provide a process wherein the solvent used in various steps can be recycled.

It is also an objective of the present invention to provide for a novel process which can be used for extraction of 14β-OH-10-DAB from any part of plants of various species of Taxus.

SUMMARY OF THE INVENTION

To meet the above objects and others, the present invention provides a novel process for the isolation of 14β-OH-10-DAB comprising preparation of an alcoholic extract of the pulverised and, optionally, dried leaves of *Taxus baccata*; preparation of a solvent extract, treatment thereof with aliphatic ketones; evaporation of the mother liquor and selective crystallisation for isolation of 10-DAB, and further treatment with aliphatic hydrocarbons for selective crystallisation and isolation of 14β-OH-10-DAB.

BRIEF DESCRIPTION OF THE FIGURE

FIG. 1 shows the compound 14B-hydroxy-10-deacetly baccatin III.

DETAILED DESCRIPTION OF THE INVENTION

The present invention provides a novel process for the isolation of 14β-OH-10-DAB which is used for the synthesis of 14β-hydroxy paclitaxel analogues. The process is simple and 14β-OH-10-DAB can be selectively isolated from the leaf extract of *T. baccata* by crystallisation. The present process involves (a) extracting the pulverised and optionally dried parts such as leaves of Taxus species, with aliphatic alcohol, (b) preparing a partially concentrated alcoholic extract containing 10-DAB, and minor quantity of 14β-OH-10-DAB, c)treating said extract with aliphatic ketones and separating the insolubles and mother liquor by centrifugation or filtration, (d) treating the residue obtain after evaporation of the mother liquor of step, (c) under vacuum with aliphatic ketone and water, the insolubles separated through celite bed by filtration or centrifugation, (e) extraction of said aqueous ketonic solution with aromatic hydrocarbons to remove coloured substances, followed by the extraction of aliphatic ester or chlorinated solvents, (f) evaporating said solution to dryness to obtain a semisolid residue from which 10-DAB is obtained by selective crystallisation, (g) isolation and purification of 10-DAB by conventional methods, (h) evaporation of mother liquor left after purification of 10-DAB and followed by treatment with aromatic hydrocarbon, and (i) isolation and purification of 14β-OH-10-DAB by conventional methods, from the residue obtained after treatment of aromatic hydrocarbon.

The process for isolation of 14β-hydroxy-10-deacetyl-baccatin III does not involve any chromatographic technique at any stage.

The preferred process comprises the following steps.

1. The leaves of *Taxus baccata* are pulverised and may be optionally dried. Water miscible aliphatic alcohol selected from methanol, ethanol, propanol, isopropanol, or tertiary butanol, is added to the ground leaves and the mixture is stirred for 12 hours. The preferred aliphatic alcohol used in the present process is methanol.

2. The semi-concentrated alcoholic extract so obtained contains 14β-OH-10-DAB and also contains 10-DAB. The extract is stirred with aliphatic ketone for one hour. The insoluble material is then separated out by filtration through celite bed or centrifugation. The liquid left behind is the mother liquor which is then used in further processing.

3. Mother liquor of step (2) is evaporated under vacuum to yield a residue which is treated with a mixture of aqueous ketonic solvent and insolubles are removed by filtration or centrifugation through a celite bed. The clear aqueous ketonic solution obtained is used for further processing.

4. The clear aqueous ketonic solution obtained is extracted with aromatic hydrocarbon to remove coloured substances other than 10-DAB. Then the remaining aqueous ketonic phase is treated with water immiscible solvent, preferably, aliphatic ester or chlorinated solvent, to extract 10-DAB along with other related compounds.

5. Thereafter, the organic solvent extract is evaporated under vacuum to dryness at 80°–90° C. to yield a semisolid residue. Subsequently, 10-DAB is selectively crystallised from the residue obtained above by treating it with aliphatic nitrile solvent such as acetonitrile, propionitrile optionally mixed with an aliphatic alcohol such as methanol, isopropanol, n-butanol or aliphatic ester such as acetone, ethylacetate, butylacetate. It is advantageous to perform the selective crystallisation in acetonitrile, optionally in the presence of ethanol, methanol or ethyl acetate, and /or butyl acetate. The 10-DAB is purified by any conventional method such as crystallisation followed by centrifugation.

6. After the crystallisation and isolation of 10-DAB, the mother liquor is enriched in 14β-OH-10-DAB. The liquor is evaporated to dryness and treated with nitrile solvent followed by aromatic hydrocarbon solvent at 80° C. for 1–2 hours. The insoluble is treated with aliphatic alcohol or aliphatic ester or chlorinated solvent and crude 14β-OH-10-DAB crystallises out. Purified 14β-OH-10-DAB may be obtained by any conventional method.

The above novel process for the isolation of 14β-OH-10-DAB can be applied for extraction from any part of the plant Taxus.sp.esp *T. baccata, T. brevifolia, T. cannadensis, T. cuspidata, T. floridara, T. media* or *T. wallichiana*. The process described above, is simple and does not involve any chromatography in at any stage and 14β-OH-10-DAB can be obtained using solvents only.

The other advantage of the present process is that the solvents used in the various steps can be reused/recycled. In addition, the applicant identified that though the raw material used in the present invention contains 10-DAB in higher quantity than 14β-DAB, the isolation of the later could be achieved without implementing chromatographic procedure.

The above novel process is described in detail by the following examples which are provided for illustration only and should not be construed to limit the scope of the present invention.

EXAMPLE I

Leaves of *Taxus baccata* are pulverised and optionally dried. Preferably, the mean particle size of the leaves is close to 0.6 mm to 0.8 mm. An alcoholic extract is prepared by stirring 1000 L of methanol with 100 kg. of the ground leaves (rotation of 58 per minute) at ambient temperature in the reactor for 12 hrs. The methanolic solution collected after centrifugation is evaporated under reduced pressure (150 m bar) at 40–50° C. in an evaporating reactor to obtain a semi concentrated extract whose weight is between 20–30% of the weight of leaves.

The 25 kg. of semiconcentrated methanolic extract containing 0.12% of 10-deacetyl baccatin-III, 20% of water and 10% of methanol (prepared under the conditions described above) is stirred (58 rpm) with 175 L. (liter) of acetone at ambient temperature for 1 to 2 hrs. The insoluble solid that appears is separated by filtration or centrifugation. The acetone soluble in mother liquor forming 35% of the weight of the semi concentrated extracted is distilled off to dryness at 40–50° C. under vacuum (150 m bar).

8.75 kg of dry residue obtained is stirred with the 43.75 L. of acetone and dimineralized water (DM) mixture (ratio preferably 2:8) for 2 hr. at ambient temperature at high rpm (72 revolution per minute). The insoluble material is removed by, filtration or centrifugation on celite bed. The aqueous ketonic mother liquor collected is clear dark red.

The aqueous ketonic layer is extracted twice with 17.5 L. and once with 8.75 L. (liter) of toluene by stirring (40 revolution per minute) for 1 hour each extraction.

The aqueous ketonic layer obtained after toluene extraction, is then extracted with methylene chloride (4×16.5 L) at ambient temperature for 30 minute each extraction by stirring at (40 revolution per minute). The methylene chloride layer is combined and dried over sodium sulphate and then evaporated to dryness under vacuum (150 m bar) at 25° to 65°0 C. in a evaporating flask.

The weight of the methylene chloride residue usually lies between 1.5 to 1.8 w/w % of the semi concentrated methanol extract, containing 4.5 to 6% of 10-deacetyl baccatin III.

EXAMPLE II 468.7 g of dry extract containing 5.1% of 10-deacetyl baccatin-III, is obtained under the conditions described in example I. The extract is stirred at 40 revolutions per for minute with 975 ml of acetonitrile at 50–60° C. When the extract is completely dissolved, the mixture is cooled at 0–5° C. for 12–16 hrs and stirred at very low rpm (20). The solid insoluble are separated out by filtration or centrifugation and washed with 50 ml of acetonitrile. A crude solid (29.43 g) is obtained after drying it at reduced pressure (0.5 m bar) at 60–70° C. for 12 hrs having 76.1% of 10-deacetyl baccatin-III.

EXAMPLE III 29.43 g of crude solid obtained under the conditions described in example II, are dissolved in 735.5 ml of methanol by refluxing at 70° C. for 1 hr with stirring (rpm –58). The solution is cooled to ambient temperature and filtered through celite bed to obtain a clear solution. The filtration is stirred at very low rpm (20) and 295 ml of acetonitrile is slowly added to it. The mixture is then cooled to 0–5° C. and maintained for 12–15 hrs. The precipitate is separated by filtration or centrifugation and washed with 10 ml mixture of methanol acetonitrile (1:1). The product is dried at reduced pressure (05 m bar) at 90–95° C. for 20–30 hr. 22.2 g of off white final product is thus obtained, containing 94.1% of 10-deacetyl baccatin-III.

The mother liquor obtained after final crystallisation is evaporated to dryness, and recycled for purification of 10-deacetyl baccatin-III.

EXAMPLE IV 30 g of crude solid obtained under the conditions described in Example II, is dissolved in 750 ml of acetone by refluxing at 65° C. for 1 to 2 hr. The solution is cooled to room temperature and then filtered through celite bed. Filtrate is stirred at very low rpm (20) and acetonitrile (300 ml) is slowly added to it. Temperature of the solution is brought down to 0–5° C. and maintained up to 15–20 hrs. The precipitate is separated out by centrifuging and the solid is washed with 1:1 mixture of acetone and acetonitrile. The final product is dried under vaccum (0.5 m bar) at temperature 80–90° C. for 12 to 20 hrs. The final (23.1 g) product is thus obtained, containing 93.5% of 10-deacetyl baccatin-III.

EXAMPLE V

After the purification of 10-deacetyl baccatin-III, the mother liquor obtained above is evaporated under vacuum (75 m bar) at 70–80° C. to dryness. The residue (35 g) obtained is then stirred with acetonitrile (350 ml) at 70–80° C. for 1 hour. The solution is chilled for 10 hours at 0–5° C. and then insoluble material is pump filtered. The mother liquor obtained is evaporated to dryness under reduced pressure (150 m bar) at 70–80° C. The residue (25 g) obtained is then stirred to 58 rpm at 80° C. with 75 ml of toluene for 1 hour. The temperature of mixture is brought down to room temperature, the toluene soluble portion is separated from toluene insoluble residue which is heated at 80° C. under vacuum to remove residual solvent. Toluene insoluble residue is then dissolved in one equivalent of methanol by stirring at 70° C. The solution is kept chilling at 0–5° C. for 24–48 hours. Crude solid is filtered and vaccum dried at 70–90° C. for 12 hours to obtain 1.9 g of solid 14β-OH-DAB.

EXAMPLE VI

The crude solid 14β-OH-10 deacetyl baccatin-III ( prepared under the conditions described in example -V) 1.9 g is dissolved in 47.5 ml of ethylacetate by refluxing for 1–2 hours. The solution is cooled to room temperature (RT) and then filtered through celite bed. The clear filtrate obtained is distilled off the solvent under vacuum (150 m bar) at 40–60° C. to reduce the volume up to 24 ml and then kept at 0–5° C. up to 12 hours. The crystallised solid is pump filtered, washed with chilled ethylacetate (2 ml) and vaccum dried at 90° C. for 12 hours, is obtained 1.28 g of furnished 14β-OH-10-deacetyl baccatin-III.

EXAMPLE VII

The crude solid of 14β-OH-10-deacetyl baccatin-III 1.9 g (prepared under the same conditions described in example -V) is dissolved in 41.8 ml of methanol by refluxing for 1 hour with stirring. The solution is cooled to room temperature (RT) and then filtered through celite bed. Clear filtrate is kept chilling at 0–5° C. for 12 hours. Crystallised solid is filtered, vacuum dried at 75–90° C. for 12 hours and thereby 1.12 g of finished 14β-OH-10-deacetyl baccatin-III is obtained.

Advantages of the Novel Process a) It is simple, cost effective and has commercial feasibility.

b) It does not involve tedious process of chromatographic technique at any stage of this process.

c) In this process, there is reusability of the solvent in many steps.

d) This process is applicable for extraction of any part of the plant of different species of Taxus.

e) This process can be used to separate paclitaxel present in the primary alcoholic extract.

f) Depending on the quality of raw material yield of 10-deacetyl baccatin-III varies from 60% to 90% of the content of raw material.

g) Though 14β-OH-DAB is present in minor quantity at the methanolic extract level, it is possible to isolate this compound without using any chromatographic technique at any stage.

We claim:

1. A process for the isolation of 14β-hydroxy-10-deacetyl bacatin-III of formula 1

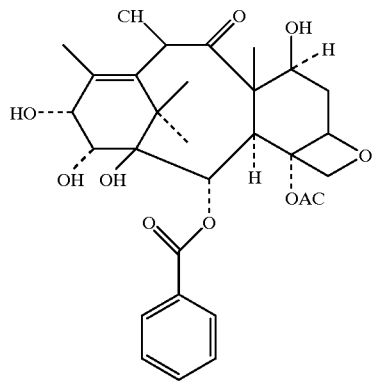

from the recoverable part of a plant of a Taxus species, said process comprising:

a) extracting the pulverised and optionally dried parts of a plant of Taxus species with aliphatic alcohol, b) preparing a partially concentrated alcoholic extract containing 10-DAB, and minor quantity of 14β-OH-10-DAB, c) treating said extract with aliphatic ketones and separating the insolubles and mother liquor by centrifugation or filtration, d) treating the residue obtained after evaporation of the mother liquor of step (c) under vacuum with aliphatic ketone and water, the insolubles separated through celite bed by filtration or centrifugation, e) extraction of said aqueous ketonic solution with aromatic hydrocarbons to remove colored substances followed by the extraction of aliphatic ester or chlorinated solvents, f) evaporating said solution to dryness to obtain a semi-solid residue from which 10-DAB is obtained by selective crystallisations, g) isolation of 10-DAB, h) evaporation of mother liquor left and followed by treatment with nitrile and aromatic hydrocarbon solvent, and i) isolation and purification of 14β-OH-10-DAB from the residue obtained after treatment of aromatic hydrocarbon.

2. A process as claimed in claim 1 wherein the aliphatic alcohol used for preparation of a alcoholic extract is selected from the group consisting of methanol, ethanol, propanol, isopropanol and tertiary butanol.

3. A process as claimed in claim 2 wherein the alcoholic extract is obtained by stirring the pulverised and optionally dried parts of the plant of the Taxus species in methanol, ethanol, propanol, isopropanol or n-butanol.

4. A process as claimed in claim 1 wherein the aqueous ketonic solution obtained in step 1 (d) is treated with aromatic hydrocarbons and followed by the extraction of aqueous ketonic layers with selected aliphatic esters or chlorinated solvents.

5. A process as claimed in claim 1 wherein 10-DAB is isolated by selective crystallisation by treatment of the residue obtained in step 1 (f) with aliphatic nitrile solvents selected from acetonitrile or propionitrile, optionally, mixed with aliphatic alcohols.

6. A process as claimed in claim 1 wherein selective crystallisation of 10-DAB is carried out by treatment of the residue with aliphatic alcohols selected from the group consisting of methanol, isopropanol, n-butanol, or aliphatic esters selected from acetone or methyl ethyl ketone.

7. A process as claimed in claim 1 wherein the alcoholic solution obtained in step 1 (a) is semi-concentrated under vaccum to at a temperature ranging from about 40° to 50° C.

8. A process as claimed in claim 1 wherein 10-DAB and 14β-OH-10-DAB is extracted from any part of any plant of the genus Taxus.

9. A process as claimed in claim 1 wherein 10-DAB can be isolated by filtration, sedimentation or centrifugation.

10. A process as claimed in claim 1 wherein the mother liquor left after isolation of 10-DAB is evaporated to dryness and treated with nitrile and aromatic hydrocarbon solvent at 80° C. for 1–2 hours.

11. A process as claimed in claim 1 wherein the insolubles are crystallised by treatment with aliphatic alcohol, aliphatic ester or chlorinated solvent.

12. A process as claimed in claim 1 wherein 14β-OH-10-DAB is isolated by filtration and crystallisation.

13. A process as claimed in claim 1 wherein 10-DAB is isolated by crystallisation followed by centrifugation.

14. A process as claimed in claim 2 wherein the aliphatic alcohol is methanol.

15. A process as claimed in claim 8 wherein the plant is *Taxus baccata*.

16. A process as claimed in claim 1 wherein the parts of the plant are the leaves.

* * * * *